United States Patent [19]

Zhu et al.

[11] Patent Number: 5,763,277
[45] Date of Patent: Jun. 9, 1998

[54] FIBER OPTIC AXIAL VIEW FLUORESCENCE DETECTOR AND METHOD OF USE

[75] Inventors: Jiazhong Zhu, Omaha, Nebr.; Arthur P. D'Silva, Ames, Iowa

[73] Assignee: Transgenomic Incorporated, Omaha, Nebr.

[21] Appl. No.: 662,467

[22] Filed: Jun. 10, 1996

[51] Int. Cl.⁶ .................................................. G01N 21/64
[52] U.S. Cl. .................. 436/172; 422/82.08; 356/344; 204/452; 204/603
[58] Field of Search .................. 356/344; 422/82.07, 422/82.08; 436/172, 180; 204/452, 603

[56] References Cited

U.S. PATENT DOCUMENTS

| | | | |
|---|---|---|---|
| 4,399,099 | 8/1983 | Buckles | 422/58 |
| 4,675,300 | 6/1987 | Fare et al. | 436/172 |
| 4,682,895 | 7/1987 | Costello | 356/402 |
| 4,740,709 | 4/1988 | Leighton et al. | 250/573 |
| 4,837,777 | 6/1989 | Jones et al. | 374/142 |
| 5,068,542 | 11/1991 | Ando et al. | 250/573 |
| 5,096,671 | 3/1992 | Kane et al. | 422/82.07 |
| 5,140,169 | 8/1992 | Evens et al. | 250/576 |
| 5,324,401 | 6/1994 | Yeung et al. | 356/344 |
| 5,484,571 | 1/1996 | Pentoney, Jr. et al. | 422/82.08 |

FOREIGN PATENT DOCUMENTS 0089157   9/1983   European Pat. Off. .

OTHER PUBLICATIONS

Axial–Beam Laser–Excited Fluorescence Detection in Capillary Electrophoresis, Taylor & Yeung, Anal. Chem. 1992, 64.

Laser Fluorescence Detector for Capillary Electrophoresis, Yeung et al., J. Chromatography, 608 (1992).

*Primary Examiner*—Jeffrey Snay
*Attorney, Agent, or Firm*—James D. Welch

[57] ABSTRACT

The present invention system includes an axially oriented end of a fiber optic present in an axially oriented system component bore in which, during use, sample analyte fluorescence is caused to occur. The present invention system and method provides that sample analyte(s) fluorescence inducing energy be entered along a path which is other than essentially parallel to the axially oriented system component bore and that detected fluorescence be transmitted to a detector by the fiber optic. A preferred source of sample analyte(s) fluorescence inducing energy is a laser system, and a preferred method by which to provide sample analyte (s) to the present invention system axially oriented system component bore involves use of electrophoresis.

13 Claims, 1 Drawing Sheet

FIBER OPTIC AXIAL VIEW FLUORESCENCE DETECTOR AND METHOD OF USE

TECHNICAL FIELD

The present invention relates to systems and methods for inducing and detecting sample analyte(s) identifying fluorescence, and more particularly is a system, and methods of use thereof, which monitors sample analyte(s) fluorescence, comprising an axially oriented fiber optic means, an end of which axially oriented fiber optic means is present within a system in which sample analyte(s) fluorescence is caused to occur by the application of energy thereto, which energy is entered along a path which is other than essentially parallel to said present axially oriented fiber optic means.

BACKGROUND

The use of fiber optic means to transport electromagnetic wavelengths is well known. In the area of chemical analysis, for instance, various Patents describe the use of fiber optics to carry electromagnetic wavelengths from a source thereof, to a system in which said electromagnetic wavelengths are caused to interact with a sample analyte. As well, various Patents describe the use of fiber optic means to carry said electromagnetic wavelengths which have interacted with said sample analyte to a detecting means. For instance, a U.S. Pat. No. 4,675,300 to Zare et al., describes a method of detecting laser excited fluorescence in an electrokinetic separation system. Said electrokinetic system involved orients a fiber optic means other than axially with respect to an orientation of a flow containing a sample analyte. It is noted that sample analyte flow is effected in the Zare et al. system by application of an electrical potential between a source of sample analyte containing solution, and an outflow container therefore.

A long path flow cell is described in U.S. Pat. No. 5,140,169 to Evens et al. Said Evens et al. system is described as a metal body containing a circular opening at each end extending perpendicularly into a center bore, adapted to receive a sample into the center bore and discharge sample from said center bore. As well, opposing fiber optic probes, each with an external sapphire window which is sealed into said metal body, are present. In use light is piped into one said fiber optic probe, caused to pass axially through said metal body, and exit via said opposing fiber optic probe. Appropriate analysis of a change effected in said light between entry and exit from said metal body allows sample analyte caused to be present in said metal body to be identified.

Another U.S. Pat. No. 5,096,671 to Kane et al., provides that light carrying optical fibers axially enter light to a system which contains a chemical sensor. Axially oriented exiting optical fibers are also present such that in use entered light is caused to interact with said chemical sensor, and then exit therethrough. Interaction with said chemical sensor effects a change in the light between entry thereto and exit therefrom, and chemicals to which the chemical sensor is sensitive affect the properties of the chemical sensor. Said 671 U.S. Pat. discloses that the sensor can operate utilizing fluorescence. In use the presence of chemicals to which the chemical sensor is sensitive can then be detected.

Another U.S. Pat. No. 4,837,777 to Jones describes a system which utilizes fiber optics to carry light axially into and out of a chamber in which the pressure or temperature can be altered. Changes in light entered to and exiting from said chamber are related to changes in pressure or temperature in said chamber.

A U.S. Pat. No. 4,399,099 to Buckles, describes a system in which an optical fiber is contained in a system into which a fluid is entered. Said fluid causes change in the optical properties of said optical fiber, and detecting changes of light caused to pass therethrough in use, before and after entry of said fluid, is related to the properties of the entered fluid.

U.S. Pat. No. 4,740,709 to Leighton et al., describes a housing with orifices present therein through which liquid is caused to flow in use. An axially oriented light source and a facing sensor are also present. Said system is utilized in measurement of optical density or light scattering measurements in a turbulently entered liquid.

U.S. Pat. No. 4,682,895 to Costello describes a system in which a fiber optic probe carries light into and out of a system. Present within said system is a sample chamber into which sample is entered during use. Said sample chamber essentially comprises a gap in said fiber optic probe pathway. In use light is entered into one end of said fiber optic probe and the light exiting said fiber optic probe is affected by what sample is placed into said sample chamber. The change in light between entry and exit from said fiber optic probe is identifying of said sample.

Another U.S. Pat. No. 5,068,542, to Ando et al., describes use of a fiber optic to intercept axially provided light produced by a laser system. The fiber optics involved are not present inside an axially oriented sample containing tube however.

Finally, a paper by Yeung et al, titled "Laser Fluorescence Detector For Capillary Electrophoresis", J. Chromatography, 608 (1992), 73–77, describes a laser-based fluorometer for use in detection in capillary electrophoresis. While laser induced fluorescence, in combination with electrophoresis mediated provision of sample analyte into the described system is reported to be a very efficient approach to sample analyte identification, the use of axially oriented optical fibers in a system for detection of sample analyte identifying fluorescence is not described.

The above discussion of known Patents and Articles shows that while the use of optical fibers in systems for use in sample analysis is known, no known system or method provides that an end of a fiber optic means should be axially oriented within a system in which sample analyte fluorescence is caused to occur by the application of energy to a present sample analyte, which energy is entered along a path which is other than essentially parallel to present, axially oriented, fiber optic means. This is particularly true where sample analyte investigated is caused to enter a sample analysis system by electrophoresis. The present invention provides such a system and methods of its use.

DISCLOSURE OF THE INVENTION

The present invention system component comprises an axially oriented system for use in inducing and measuring sample analyte identifying fluorescence. Said axially oriented system component comprises an axially oriented system bore therethrough, and further comprises a fiber optic means, an axially oriented end of said fiber optic means being present within said axially oriented system component bore. During use, sample analyte fluorescence is caused to occur by the application of energy to sample analyte(s) caused to be present within said axially oriented system component bore, with said fluorescence inducing energy being entered to said axially oriented system component bore along a path which is other than essentially parallel to said axially oriented system component axial orientation. Produced fluorescence enters said axially oriented end of said fiber optic means present within said axially oriented system component bore, and is transmitted by said fiber optic means to a detector system located distally along said fiber optic means.

The present invention axially oriented system component is typically essentially tubular in shape with means for entry and exit of sample analyte, (typically in a solution form), present at ends thereof. In addition, it is noted that the entire axially oriented system component can be transparent to fluorescence producing energy, or only a window in said axially oriented system component might be transparent to fluorescence producing energy. In the later case said transparent window is located such that fluorescence producing energy entered therethrough is provided to said axially oriented system near the location of the axially oriented end of said fiber optic means present in said axially oriented system component bore.

A preferred embodiment of the present invention further comprises a sample solution containing system source of sample analyte(s) and a sample solution receiving system. In use said axially oriented system component bore is caused to be filled with a sample analyte(s) containing sample solution, and sample analyte(s) containing sample solution present at one end of said axially oriented system component is caused to be continuous with a sample analyte containing sample solution present in said sample solution containing system source of sample analyte, while sample analyte(s) present at an axially distal end of said axially oriented system component is caused to be continuous with sample analyte containing sample solution present in said sample solution receiving system. Said configuration, it will be appreciated is appropriate for use in an electrophoresis scenario wherein an electric potential is applied between said sample analyte containing solution in said sample solution containing system source of sample analyte and a sample solution receiving system, such that sample analyte(s) present therein are caused to migrate through said axially oriented system component bore.

A method of producing and accessing for analysis, sample analyte identifying fluorescence can involve:

a. providing an axially oriented system component as described infra;

b. causing sample analyte(s) to be present in said axially oriented system component bore;

c. causing sample analyte(s) fluorescence inducing energy to be entered to said axially oriented system component along a path which is other than essentially parallel to said axial orientation;

such that produced fluorescence enters said axially oriented end of said fiber optic means present within said axially oriented system component, and is transmitted by said fiber optic means to a detector system located distally along said fiber optic means.

Said described method of producing and accessing for analysis, sample analyte identifying fluorescence, in a preferred embodiment, provides that the step c. act of causing sample analyte(s) fluorescence inducing energy enter said fluorescence inducing energy along a path which is essentially perpendicular to said axially oriented system component axial orientation.

A more detailed method of producing, and accessing for analysis, sample analyte identifying fluorescence, applicable in an electrophoresis setting, comprises the steps of:

a. providing an axially oriented system component as described infra, including said sample solution containing system source of sample analyte(s), and a sample solution receiving system;

b. causing a sample analyte(s) containing sample solution to be continuously present within said axially oriented system component bore, said sample solution containing system source of sample analyte(s) and said sample solution receiving system;

c. applying an electric potential between sample analyte(s) containing sample solution present in said sample solution containing system source of sample analyte(s) and said sample solution receiving system;

d. causing sample analyte(s) fluorescence inducing energy to be entered to said axially oriented system component along a path which is other than essentially parallel to said axial orientation;

such that produced fluorescence enters said axially oriented end of said fiber optic means present within said axially oriented system component, and is transmitted by said fiber optic means to a detector system located distally along said fiber optic means.

Again, said described method of producing and accessing for analysis, sample analyte identifying fluorescence, in a preferred embodiment, provides that, the step d. act of causing sample analyte(s) fluorescence inducing energy enter said fluorescence inducing energy along a path which is essentially perpendicular to said axially oriented system component axial orientation.

A preferred source of sample analyte fluorescence inducing energy should be understood to include laser systems.

The present invention system will be better understood by reference to the Detailed Description Section of this Disclosure, with reference being had to the accompanying Drawings.

SUMMARY OF THE INVENTION

It is a primary purpose of the present invention to provide a system and methods of use thereof, for inducing and detecting sample analyte(s) identifying fluorescence.

It is a particular purpose of the present invention to disclose a system which includes a fiber optic means, an end of which fiber optic means is axially oriented within a system component in which sample analyte fluorescence is caused to occur, by the application of energy to present sample analyte(s) is disclosed.

It is yet another particular purpose of the present invention to disclose that sample analyte(s) fluorescence inducing energy should be entered along a path which is other than essentially parallel to, axially oriented, fiber optic means in a present invention axially oriented system component.

It is still yet another purpose of the present invention to teach that a preferred source of sample analyte(s) fluorescence inducing energy includes lasers.

It is still yet another purpose of the present invention to describe that a preferred method by which to provide sample analyte(s) to the present invention system component involves electrophoresis.

DETAILED DESCRIPTION

Figure 1:
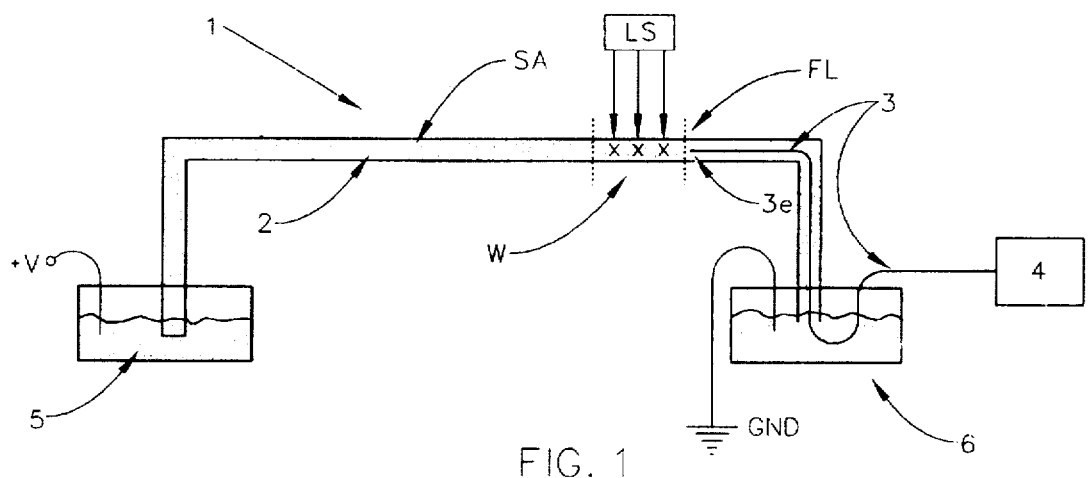
FIG. 1 shows an axially oriented system component of the present invention, including an axially oriented fiber optic means.
Figure 2:
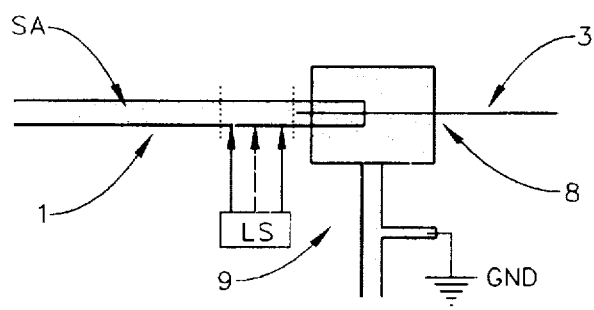
FIG. 2 shows an axially oriented optical fiber means axially entered to a present invention axially oriented system component, via a sealed or sealable means.

Turning now to the Drawings, there is shown in FIG. 1 a present invention axially oriented system component (1) for use in inducing and measuring sample analyte (SA) identifying fluorescence (FL). Said axially oriented system (1) comprises an axially oriented system bore (2) therethrough, and further comprises a fiber optic means (3), an axially oriented end (3e) of which fiber optic means (3) is present within said axially oriented system component bore (2). It should be noted that said fiber optic means (3) is threaded into the axially oriented system component bore (2) from an open right oriented side thereof, through which sample solution flows in use. This demonstrates a preferred embodiment. However, as shown in FIG. 2, it is to be understood that said axially oriented fiber optic means (3) could be entered through a sealed or sealable opening (8) in a retaining means (9) for said axially oriented system component (3), such that said fiber optic means (3) is entered thereto directly in line with said axially oriented system component bore (2). Such a configuration is within the scope of the present invention system.

Referring again to FIG. 1, during use, sample analyte fluorescence (FL) is caused to occur by the application of energy (LS) to sample analyte(s) (SA) which are caused to be present within said axially oriented system component bore (2), with said fluorescence (FL) inducing energy, (LS) being entered to said axially oriented system component bore (2) along a path which is other than essentially parallel to said axially oriented system component (1) axial orientation. Produced fluorescence (FL) enters said axially oriented end (3e) of said fiber optic means (3) present within said axially oriented system component bore (2), and is transmitted by said fiber optic means to a detector system (4) located distally along said fiber optic means (3).

The present invention axially oriented system component (1) is typically essentially tubular in shape with means for entry of sample analyte, (SA), typically in a solution form, present at ends thereof. In addition, it is noted that the entire axially oriented system component (1) can be transparent to fluorescence (FL) producing energy (LS), or only a window (W) in said axially oriented system component (1) might be transparent to fluorescence (FL) producing energy (LS). In the later case said transparent window (W) is located such that fluorescence (FL) producing energy (LS) entered therethrough is provided to said axially oriented system component (1) near the location of the axially oriented end (3e) of said fiber optic means (3) present in said axially oriented system component bore (2).

A preferred embodiment of the present invention further comprises a sample solution containing system source of sample analyte(s) (5) and a sample solution receiving system (6). In use said axially oriented system component bore (2) is caused to be filled with a sample analyte(s) (SA) containing sample solution, and sample analyte(s) (SA) containing sample solution present at one end of said axially oriented system component (1) is caused to be continuous with a sample analyte containing sample solution present in said sample solution containing system source of sample analyte (5), while sample analyte(s) present at an axially distal end of said axially oriented system component is caused to be continuous with sample analyte containing sample solution present in said sample solution receiving system (6). Said configuration, it will be appreciated is appropriate for use in an electrophoresis scenario wherein an electric potential (V+) is applied to said sample analyte containing solution in said sample solution containing system source of sample analyte (5) and a ground potential (GND) is applied to said sample solution receiving system (6), such that sample analyte(s) (SA) present therein are caused to migrate through said axially oriented system bore (2). Sample analytes will be caused to transverse the length of the axially oriented system component (1) at rates dependent upon, for instance, charge and mass thereof.

Figure 3:
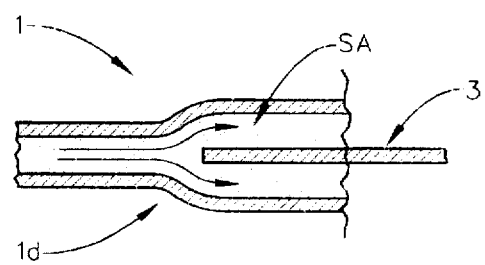
FIG. 3 shows an shows an axially oriented system component of the present invention, including an axially oriented fiber optic means, in which the inner diameter of the axially oriented system component is increased at the location of contained axially oriented fiber optic means.

FIG. 3 shows that the axially oriented system component (1) can provide an increased inner diameter (1d) at the point at which the fiber optic means (3) enters thereto. Said increased inner diameter (1d) provides a non-constricted annular space in which sample analyte (SA) containing sample solution (5) can flow, in the presence of said fiber optic means (3).

Figure 4:
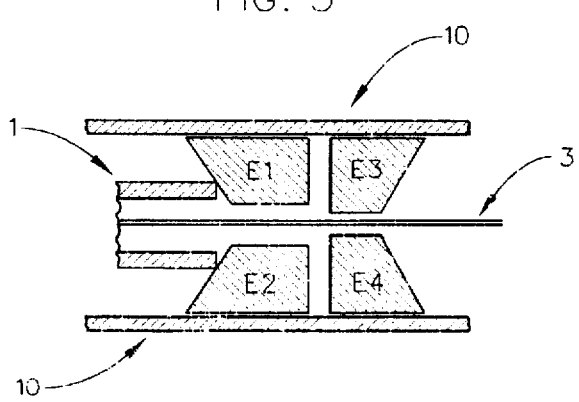
FIG. 4 shows an alignment system means by which the axially oriented system component and the fiber optice means can be easily aligned in use.

FIG. 4 shows an alignment system means by which the axially oriented system (1) and the fiber optic means (3) can be easily aligned in use. Shown are elements (E1), (E2), (E3) & (E4) Each of said elements presents with an angled surface which in use is caused to face the entry of the axially oriented system (1) or the fiber optic means (3), by position retention mounting in securing means (10). Note that angled surfaces of elements (E1) & (E2) provide centering of an axially oriented system (1) entered thereto, and angled surfaces of elements (E3) & (E4) provide centering means for fiber optic means (3) entered thereto. Note that the centering effect of elements (E3) & (E4) provides the fiber optic means (3) centrally in the axially oriented system (1). That is, the vertically shown length of element (E4) is greater than that of element (E2). In use a user can then easily enter fiber optic means (3) to axially oriented system (1) by simple laterally imposed motion of each, as viewed in FIG. 4.

Methods of producing and accessing for analysis, sample analyte identifying fluorescence, are described in the Disclosure of the Invention Section of this Disclosure.

It is to be understood that preferred sources of fluorescence (FL) producing energy (LS) include laser systems.

It is to be understood that terminology "axially oriented system" can mean a capillary tube with an inner "bore" diameter on the order of, for instance, approximately one-hundred (100) microns, and the terminology "fiber optic means" can mean an accompanying electromagnetic wavelength transmitting means with an outer diameter of, for instance, seventy-five (75) microns diameter or less.

It is to be understood that the terminology "essentially tubular" can include tube shapes other than circular cross-sections.

Having hereby disclosed the subject matter of the present invention, it should be obvious that many modifications, substitutions, and variations thereof are possible in light thereof. It is therefore to be understood that the present invention can be practiced other than as specifically described, and should be limited in breadth and scope only by the claims.

I claim:

1. A system for use in inducing and measuring sample analyte identifying fluorescence, said system comprising an axially oriented system component with a bore present therethrough, said axially oriented system component further comprising a fiber optic means, an axially oriented end of which fiber optic means is present within said axially oriented system component bore; in which axially oriented system component bore, during use, sample analyte fluorescence is caused to occur by the application of energy to sample analyte(s) caused to be present within said axially oriented system component bore;

> said system for use in inducing and measuring sample analyte identifying fluorescence further comprising a source of fluorescence inducing energy and a detector system, said source of fluorescence inducing energy being positioned and oriented with respect to said axially oriented system component so that fluorescence inducing energy provided thereby is, in use, caused to enter said axially oriented system component bore along a path which is other than essentially parallel to said axially oriented system component bore, and said detector being positioned so as to receive an end of said fiber optic means located distally from said axially oriented end of which fiber optic means present within said axially oriented system component bore;
>
> such that in use fluorescence inducing energy is caused to be entered to said axially oriented system bore along a path which is other than essentially parallel to said axially oriented system component bore, and such that fluorescence produced by interaction with sample analyte(s) caused to be present in said axially oriented system component bore, enters said axially oriented end of said fiber optic means present within said axially oriented system bore, and is transmitted by said fiber optic means to said detector system which is located distally along said fiber optic means, in which detector system said produced sample analyte identifying fluorescence is measured.

2. A system for use in inducing and measuring sample analyte identifying fluorescence as in claim 1, in which said axially oriented system component is essentially tubular in shape with means for entry and exit of sample analyte present at ends thereof.

3. A system for use in inducing and measuring sample analyte identifying fluorescence as in claim 1, in which the entire axially oriented system component is transparent to energy with wavelengths present in said fluorescence inducing energy as the result of said entire axially oriented system component being made of a material which does not significantly absorb energy with wavelengths present in said fluorescence producing energy.

4. A system for use in inducing and measuring sample analyte identifying fluorescence as in claim 1, in which only a window in said axially oriented system component is transparent to energy with wavelengths present in said fluorescence inducing energy as the result of only said window being made of a material which does not significantly absorb energy with wavelengths present in said fluorescence inducing energy, said window being located such that fluorescence inducing energy entered therethrough is provided to said axially oriented system component near the location of the axially oriented end of said fiber optic means present in said axially oriented system component bore.

5. A system for use in inducing and measuring sample analyte identifying fluorescence as in claim 1, which further comprises a sample solution containing system source of sample analyte(s) and a sample solution receiving system, such that in use said axially oriented system component bore is caused to be filled with a sample analyte(s) containing sample solution, and such that sample analyte(s) containing sample solution present at one end of said axially oriented system component is caused to be continuous with a sample analyte containing sample solution present in said sample solution containing system source of sample analyte, and such that sample analyte(s) present at an axially distal end of said axially oriented system component is caused to be continuous with sample analyte containing sample solution present in said sample solution receiving system; such that in use an electric potential is applied between said sample analyte containing solution present in said sample solution containing system source of sample analyte, and that present in said sample solution receiving system, such that sample analyte(s) present are caused to migrate through said axially oriented system component bore by electrophoresis.

6. A system for use in inducing and measuring sample analyte identifying fluorescence as in claim 1 in which said axially oriented system component bore presents with an increased inner diameter whereat said axially oriented end of said fiber optic means is present therewithin, as compared to the inner diameter of said axially oriented system component bore at locations where said fiber optic means is not present therewithin.

7. An axially oriented system for use in inducing and measuring sample analyte identifying fluorescence as in claim 1, in which said source of fluorescence inducing energy is positioned with respect to said axially oriented system component bore such that fluorescence inducing energy is entered to said axially oriented system component bore along a path which is essentially perpendicular to said axially oriented system component bore orientation.

8. A method of inducing and accessing sample analyte identifying fluorescence for analysis, comprising the steps of:

a. providing a system for use in inducing and measuring sample analyte identifying fluorescence, said system comprising an axially oriented system component with a bore present therethrough, said axially oriented system component further comprising a fiber optic means, an axially oriented end of which fiber optic means is present within said axially oriented system component bore; in which axially oriented system component bore, during use, sample analyte fluorescence is caused to occur by the application of energy to sample analyte(s) caused to be present within said axially oriented system component bore;

> said system for use in inducing and measuring sample analyte identifying fluorescence further comprising a source of fluorescence inducing energy and a detector system, said source of fluorescence inducing energy being positioned and oriented with respect to said axially oriented system component so that fluorescence inducing energy provided thereby is, in use, caused to enter said axially oriented system component bore along a path which is other than essentially parallel to said axially oriented system component bore, and said detector being positioned so as to receive an end of said fiber optic means located distally from said axially oriented end of which fiber optic means present within said axially oriented system component bore;
>
> such that in use fluorescence inducing energy is caused to be entered to said axially oriented system bore along a path which is other than essentially parallel to said axially oriented system component bore, and such that fluorescence produced by interaction with sample analyte(s) caused to be present in said axially oriented system component bore, enters said axially oriented end of said fiber optic means present within said axially oriented system bore, and is transmitted by said fiber optic means to said detector system which is located distally along said fiber optic means, in which detector system said produced sample analyte identifying fluorescence is measured;

b. causing sample analyte(s) to be present in said axially oriented system component bore;

c. causing sample analyte(s) fluorescence inducing energy to be entered to said axially oriented system component bore along a path which is other than essentially parallel to said axially oriented system component bore;

such that induced fluorescence enters said axially oriented end of said fiber optic means present within said axially oriented system component bore, and is transmitted by said fiber optic means to a detector system located distally along said fiber optic means.

9. A method of inducing and accessing sample analyte identifying fluorescence for analysis as in claim 8, in which the step c. act of causing sample analyte(s) fluorescence inducing energy to be entered to said axially oriented system component bore involves positioning said source of fluorescence inducing energy such that said fluorescence inducing energy is entered along a path which is essentially perpendicular to said axially oriented system component bore.

10. A method of inducing and accessing sample analyte identifying fluorescence for analysis as in claim 8, in which the step c. act of causing sample analyte(s) fluorescence inducing energy to be entered to said axially oriented system component involves the use of a laser.

11. A method of inducing and accessing sample analyte identifying fluorescence for analysis, comprising the steps of:

a. providing a system for use in inducing and measuring sample analyte identifying fluorescence, said system comprising an axially oriented system component with a bore present therethrough, said axially oriented system component further comprising a fiber optic means, an axially oriented end of which fiber optic means is present within said axially oriented system component bore; in which axially oriented system component bore, during use, sample analyte fluorescence is caused to occur by the application of energy to sample analyte(s) caused to be present within said axially oriented system component bore;

said system for use in inducing and measuring sample analyte identifying fluorescence further comprising a source of fluorescence inducing energy and a detector system, said source of fluorescence inducing energy being positioned and oriented with respect to said axially oriented system component so that fluorescence inducing energy provided thereby is, in use, caused to enter said axially oriented system component bore along a path which is other than essentially parallel to said axially oriented system component bore, and said detector being positioned so as to receive an end of said fiber optic means located distally from said axially oriented end of which fiber optic means present within said axially oriented system component bore, such that in use fluorescence inducing energy is caused to be entered to said axially oriented system bore along a path which is other than essentially parallel to said axially oriented system component bore, and such that fluorescence produced by interaction with sample analyte(s) caused to be present in said axially oriented system component bore, enters said axially oriented end of said fiber optic means present within said axially oriented system bore, and is transmitted by said fiber optic means to said detector system which is located distally along said fiber optic means, in which detector system said produced sample analyte identifying fluorescence is measured;

said system for use in inducing and measuring sample analyte identifying fluorescence further comprising a sample solution containing system source of sample analyte(s) and a sample solution receiving system, such that in use said axially oriented system component bore is caused to be filled with a sample analyte(s) containing sample solution, and such that sample analyte(s) containing sample solution present at one end of said axially oriented system component is caused to be continuous with a sample analyte containing sample solution present in said sample solution containing system source of sample analyte, and such that sample analyte(s) present at an axially distal end of said axially oriented system component is caused to be continuous with sample analyte containing sample solution present in said sample solution receiving system; such that in use an electric potential is applied between said sample analyte containing solution present in said sample solution containing system source of sample analyte, and that present in said sample solution receiving system, such that sample analyte(s) present are caused to migrate through said axially oriented system component bore by electrophoresis;

b. causing a sample analyte(s) containing sample solution to be continuously present within said axially oriented system component bore, a sample solution containing system source of sample analyte(s) and a sample solution receiving system;

c. applying an electric potential between sample analyte(s) containing sample solution present in said sample solution containing system source of sample analyte(s), and said sample solution receiving system;

d. causing sample analyte(s) fluorescence inducing energy to be entered to said axially oriented system component bore along a path which is other than essentially parallel to said axially oriented system component bore;

such that induced fluorescence enters said axially oriented end of said fiber optic means present within said axially oriented system component bore, and is transmitted by said fiber optic means to said detector system located distally along said fiber optic means.

12. A method of inducing and accessing sample analyte identifying fluorescence for analysis as in claim 11, in which the step d. act of causing sample analyte(s) fluorescence inducing energy to be entered to said axially oriented system component bore involves positioning said source of fluorescence inducing energy such that said fluorescence inducing energy is entered along a path which is essentially perpendicular to said axially oriented system component bore.

13. A method of inducing and accessing sample analyte identifying fluorescence for analysis as in claim 11, in which the step d. act of causing sample analyte(s) fluorescence inducing energy to be entered to said axially oriented system component involves the use of a laser.

* * * * *